United States Patent [19]

Youngdale

[11] 4,288,440

[45] Sep. 8, 1981

[54] PYRIDINONES

[75] Inventor: Gilbert A. Youngdale, Portage, Mich.

[73] Assignee: The Upjohn Company, Kalamazoo, Mich.

[21] Appl. No.: 182,554

[22] Filed: Aug. 29, 1980

[51] Int. Cl.³ .................. C07D 213/64; C07D 213/48; C07D 401/04; A61K 31/41

[52] U.S. Cl. .................................. 424/263; 546/276; 546/298

[58] Field of Search ................ 546/298, 276; 424/263

[56] References Cited

U.S. PATENT DOCUMENTS

| | | | |
|---|---|---|---|
| 3,378,564 | 4/1968 | Holland | 546/276 |
| 4,104,273 | 8/1978 | McNulty | 546/298 |
| 4,220,648 | 9/1980 | Youngdale | 546/298 |

FOREIGN PATENT DOCUMENTS

| | | |
|---|---|---|
| 2637477 | 8/1976 | Fed. Rep. of Germany . |
| 2635206 | 2/1978 | Fed. Rep. of Germany . |

OTHER PUBLICATIONS

J. Org. Chem. 11:741, (1946), Geissman et al.
Monatsh Chem. 106:963, (1975), Ollinger et al.
Acta Chem. Scand. B30:863, (1976), Becher et al.
A. F. Holland and J. N. Peseira, J. Med. Chem., 10:149, (1967).
Fang, V. S., Arch. Int. Pharmacodyn, 176:193, (1968).
J. Heterocyl. Chem. 9:165, (1972), Bonnetand et al.
Biochemistry 10:2313, (1971), Guilbert et al.
Acta Chem. Scand. B31:843, (1977), Becher et al.
Chem. Pharm. Bull. 22:763, (1974), Sugasawa et al.
Can. J. Chem. 56:613, (1978), Findlay et al.

*Primary Examiner*—John M. Ford
*Attorney, Agent, or Firm*—Robert A. Armitage; Lawrence T. Welch

[57] ABSTRACT

The present invention relates to certain 6-alkyl-1,2-dihydro-2-oxo-3-substituted pyridine derivatives, their preparation and antihyperglycemic use.

15 Claims, No Drawings

PYRIDINONES

DESCRIPTION

1. Technical Field

The present invention provides novel organic compounds. In particular, the present invention provides compounds structurally related to pyridine. Most particularly, the present invention relates to certain 1,2-dihydro-2-oxo-3-substituted-pyridine compounds.

The present invention further relates to novel methods for the synthesis and use of the novel organic compounds disclosed herein. These novel methods for use relate to the antihyperglycemic effect of administration of the novel organic compounds of the present invention.

The compounds of the present invention are derivatives of 1,2-dihydro-2-oxo-pyridine or 2-pyridinone. The structure and carbon atom numbering for this compound is indicated by Formula I. The compounds of the present invention have an alkyl group at the six position and a carboxaldehyde or tetrazole group at the three position.

As indicated above, the present invention also relates to antihyperglycemia agents. Hyperglycemia refers to a condition commonly found in patients suffering from mature-onset diabetes mellitus and other diseases in which impairment of pancreatic function is a consequence thereof. Accordingly, hyperglycemic patients are those exhibiting elevated serum glucose levels. Failure to adequately control such elevated serum glycose levels has been associated in such patients with untoward cardiovascular effects (myocardioischemia, stroke, and peripheral vascular diseases), lethargy, coma, and even death.

While conventional treatment for these hyperglycemic conditions may include diet (e.g., restriction of carbohydrate intake) and insulin injection, one important means of treating such patients is with oral antihyperglycemic agents. The most important class of oral antihyperglycemic agents is sulfonylureas, e.g., tolbutamide, clorpropamide, tolazamide, and glyburide.

As oral antihyperglycemic agents, sulfonylureas have as a primary mechanism of action the induction of endogenous insulin release. Accordingly, these compounds exhibit activity in glucose-primed, fasted, intact rats and glucose-primed, fasted, adrenalectomized rats. However, in other animal preparations, e.g., alloxanized diabetic and eviscerate rats, no anti-hyperglycemic effect is observed.

Another class of oral antihyperglycemic agents is biguanidines, principally phenformin. Unlike the sulfonylureas, the biguanidines do not stimulate endogenous insulin secretion, but are nonetheless effective in lowering elevated blood glucose levels in mature onset diabetics. In non-diabetic subjects, however, no significant antihyperglycemic effect is ordinarily observed upon biguanidine administration.

Yet another class of oral antihyperglycemic agents is represented by certain nicotinic acid derivatives, particularly 1,2-dihydro-2-oxonicotinic acid derivatives. Such compounds are, for example, disclosed in German Offenlegungsschrift No. 2,637,477, published Aug. 20, 1976, abstracted at Derwent Number 16112A. The tautomeric form of 1,2-dihydro-2-oxo-nicotinic acid, 2-hydroxynicotinic acid has been demonstrated to have antihyperglycemic activity in the alloxanized diabetic rat, but this activity has been associated with a decrease of plasma-free fatty acids. See Fang, V. S., Arch. Int. Pharmacodyn, 176:193 (1968).

2. Prior Art

Orally active antihyperglycemic agents are widely known in the art, as indicated by references cited above.

For example, see the references cited above relating to 1,2-dihydronicotinic acids. See, also, applicant's co-pending application Ser. No. 005,454, and references cited therein.

A number of 1,2-dihydro-2-oxo-3-pyridinecarboxaldehydes are reported in the literature. None have been disclosed for hypoglycemic uses, and the chemistry of their synthesis is quite dissimilar to the synthesis of compounds of the present invention. See, e.g., J. Heterocyl. Chem. 9:165 (1972); Biochemistry 10:2313 (1971); Acta Chem. Scand. B31:843 (1977); Chem. Pharm. Bull. 22:763 (1974); Can. J. Chem. 56:613 (1978); J. Org. Chem. 11:741 (1946); Monatsh Chem. 106:963 (1975); Acta Chem. Scand. B30:863 (1976) and German Offenlegunsschrift No. 2,635,206, abstracted at Derwent Number 10271A/06.

A 6-methyl-1,2-dihydro-2-oxo-3-pyridinctetrazole is reported by A. F. Holland and J. N. Peseira, J. Med. Chem., 10:149 (1967). It is stated to be active as an inhibitor of norepinephrine-induced release of free fatty acids. No other biological activity is disclosed.

SUMMARY OF THE INVENTION

The present invention particularly relates to novel organic compounds.

The present invention further relates to the pharmacological use of such compounds.

The present invention further relates to novel pharmaceutical compositions employing these compounds. In particular, the present invention provides:

A. A compound of Formula II wherein $R_1$ is alkyl of four to eight carbon atoms, inclusive, and $R_2$ is tetrazolyl or carboxaldehyde.

B. A method of treating adult onset diabetes mellitus in a human suffering from said disease which comprises orally administering an amount of a compound of the Formula II, or a pharmacologically acceptable amine cation thereof, wherein $R_1$ and $R_2$ are defined as above, effective to exert a predetermined systemic antihyperglycemic effect.

C. An oral pharmaceutical composition in unit dosage form comprising an amount of a compound of the Formula II wherein $R_1$ and $R_2$ are as defined above, sufficient to provide an antihyperglycemic effect in an adult-onset diabetic human to whom said composition is administered.

The novel compounds of the present invention are all antihyperglycemic agents, particularly oral antihyperglycemic agents. This antihyperglycemic activity renders these compounds useful in the treatment of adult-onset diabetes mellitus. Adult-onset diabetes mellitus is a disease characterized by pancreatic dysfunction resulting in insufficient levels of insulin being produced or secreted by the pancreas. This form of diabetes mellitus is distinguished from other pancreatic disorders wherein the capacity of the pancreas to produce insulin is totally abolished. While oral antihyperglycemic agents are uniformly ineffective in treating the latter pancreatic diseases, well-known and well-recognized methods exist in the art for the treatment of adult-onset diabetes mellitus with oral antihyperglycemic agents.

The novel compounds of the present invention are all used in the treatment of adult-onset diabetes mellitus by these well-known and well-recognized methods in the art. Accordingly, a patient to be treated with the novel compounds of the instant invention is first diagnosed as a diabetic by conventional means (e.g., the persistence of elevated serum glucose levels), and a treatment regimen with the compounds of the present invention is established so that the elevation in a patient's serum glucose level is either significantly reduced or eliminated. Precise therapeutic endpoint of the treatment (i.e., elimination or merely reduction in hyperglycemia) is readily determined by the attending physician based upon the clinical presentation and concomitantly employed treatment. For example, the novel compounds of the instant invention may be employed to significantly reduce hyperglycemia in a patient, with a carbohydrate-restricted diet providing the further measure of control.

While the novel compounds of the instant invention may be administered by any convenient systemic route, these compounds are most significantly and usefully employed as oral antihyperglycemic agents, particularly in solid dosage forms (e.g., capsules and tablets). Alternatively, liquid oral dosage forms (e.g., syrups and elixirs) are alternatively employed. The solid, oral pharmaceutical compositions in accordance with the present invention are all prepared by methods known in the art, e.g., methods for preparing other oral antidiabetic compositions. These pharmaceutical compositions are all prepared by methods well known in the art.

Since an individual patient response to treatment with compounds in accordance with the present invention may vary, effective dosages of the compounds of the instant invention will vary from patient to patient. Ordinarily, an oral dosage of 1 mg/kg of a compound in accordance with the instant invention will be adequate to significantly reduce hyperglycemia in patients being treated. Repeated dosages (e.g., every four to twelve hours) may be required during the day to maintain the antihyperglycemic effect. Accordingly, dosages in accordance with the present invention may range from as low as about 0.1 mg/kg/dose to as high as about 10 mg/kg/dose, depending upon the patient, frequency of treatment, and observed response. In accordance with well-recognized methods, an attending physician may at first prescribe a relatively small amount of the novel 1,2-dihydro-2-oxo-3-substituted pyridine derivative with subsequent increases in this dosage as necessary to achieve the desired level of control.

The novel 6-alkyl-1,2-dihydro-2-oxo-3-substituted pyridine derivatives of the present invention are prepared in accordance with the procedures depicted in Chart A, wherein all variables are as defined above.

The formula XIII compound of Chart A is prepared from the formula XI compound via the formula XII 1,2-dihydro-2-oxo-6-alkyl-3-cyano-pyridine intermediate. The formula XII intermediate can be prepared using well known procedures. See, e.g., Mariella, Organic Synthesis, 4:210 (1963) Kochetkov, Doklady Akad. Nauk. S.S.S.R., 84:2289 (1952); and Binovi and Arlt, J. Org. Chem. 26:1656 (1961). The process depicted in Chart A is that of Perez-Medina, et al., J. Am. Chem. Soc. 69:2574 (1974) and that set forth in Example 1, parts A and B.

To prepare compounds of the formula XIII wherein $R_2$ is tetrazole, the formula XII intermediate is reacted with sodium azide, ammonium chloride and lithium chloride in an inert solvent.

To prepare compounds of the formula XIII wherein $R_2$ is carboxaldehyde, the formula XII intermediate is reacted in the presence of a Raney Nickel catalyst with formic acid or with sodium hypophosphite in aqueous acetic acid in pyridine.

DESCRIPTION OF THE PREFERRED EMBODIMENTS

Compounds in accordance with the instant invention are all prepared in accordance with the representative examples provided below:

EXAMPLE 1

6-Neopentyl-3-(1H-tetrazol-5-yl)-2-(1H)-pyridinone (Formula XIII of Chart A: $R_1$ is neopentyl and $R_2$ is tetrazolyl)

A. Sodium salt of 3-oxo-5,5-dimethylhexanyl (Formula XI of Chart A) $R_1$ is neopentyl A mixture of 142 ml (115 g, 1 mole) of 4,4-dimethyl-2-pentanone and 82 ml (74 g, 1 mole) of ethyl formate is added dropwise during 1.5 hr to a stirred mixture of 3 l of dry toluene, 3 ml (2.3 g, 0.05 mole) of absolute ethyl alcohol, and 48 g of 50% sodium hydride dispersion in mineral oil (24 g, 1 mole of sodium hydride). A bubbler is used to observe hydrogen gas evolution. The initial temperature is about 23° C. The mixture is cooled occasionally during the addition to keep the temperature at approximately 30° C. A solid separates during the addition. After the addition is completed an additional 500 ml of toluene is added to facilitate the stirring. The mixture is stirred for approximately twenty-four hr. The solid is collected by filtration, washed with toluene, and dried under vacuum at 56° for nineteen hours giving 148.4 g (90%) of the product as an ivory solid. Some solid separates in the combined filtrate and washing upon standing. NMR absorptions are observed at 0.98, 2.3, 4.61, 5.21, 8.8–9.06δ

B.

1,2-Dihydro-2-oxo-6-neopentyl-3-pyridinecarbonitrile (Formula XII of Chart A: $R_1$ is neopentyl)

A mixture of 32.6 g (388 mmoles) of cyanoacetamide, 63.8 g of the product of Part A and 600 ml of dioxane is stirred and heated under reflux for twenty hrs. Initially neither the product of Part A nor the cyanoacetamide is soluble in the dioxane at room temperature. As the heating commences the mixtures become red and most of the material is dissolved. Then solid begins separating. After cooling the mixture the solid is collected by filtration and washed with a small amount of dioxane. The solid is dissolved in 1 l of water and acidified with 24 ml of acetic acid. A solid separates. The mixture is extracted with ethyl acetate (2×750 ml). The combined extracts are washed with 200 ml of water and 100 ml of brine and dried over magnesium sulfate. Evaporation of the solvent leaves 25.6 g of yellow-brown solid. The majority of the dioxane is evaporated from the combined filtrate and washing, leaving a red-brown viscous oil. The oil is slurried with 1 liter of water. Most of the material dissolves. The mixture is acidified with 24 ml of acetic acid. A brown viscous oil separates. The mixture is extracted with ethyl acetate (2×750 ml). The combined extracts are washed with 200 ml of water and 100 ml of brine and dried over magnesium sulfate. Evaporation of the solvent leaves 43 g of dark red viscous oil. The 43 g of oil is chromatographed on a 1.3 kg column of silica gel. The column is eluted with 10% acetone-methylene chloride and 200 ml fractions are collected. The fractions are assayed by silica gel TLC (1×4") (20% acetone-methylene chloride solvent system) and crystallized material is assayed by silica gel TLC (1×4") (60% ethyl acetate-Skellysolve B). Fractions 21–38 are combined and crystallized from acetone-Skellysolve B giving 4.28 g of buff solid, having a melting point of 207°–208° C. Concentration of the filtrate gives a sticky solid which is crystallized from acetone-Skellysolve B giving 0.78 g of buff solid having a melting point of 207°–208° C. The total yield from this column is 5.6 g (6.8%).

The 25.6 g of the solid obtained above is chromatographed on a 1.3 kg column of silica gel. The column is eluted with 10% acetone-methylene chloride and 200 ml fractions are collected. The fractions and crystallized material are assayed in the same manner as used for the first column. Fractions 19–57 are combined and crystallized from acetonehexane giving 15.25 g of white needles having a melting point of 209°–210° C. Concentration of the filtrate gives 3.6 g of ivory solid having a melting point of 207°–208° C. Evaporation of the solvent from the filtrate leaves a solid which is crystallized twice from acetone-Skellysolve B giving 0.59 g of ivory solid having a melting point of 207°–208.5° C. The total yield from this column is 19.44 g (26.3%). The total yield for the reaction is 24.5 g (33.1%). A portion of the 15.25 g is submitted for analysis. Carbon:Hydrogen:Nitrogen analyses for the compound is 69.50:7.61:14.42. Mass Spectrum exhibits peaks at 190, 175, 135, 134, 116, 64, 57, 41, 39, and 29. NMR absorptions are observed at 1.01, 2.59, 6.19, 7.81, 13.4–13.6δ. Infrared absorptions are observed at 3140, 3120, 3080, 2950, 2220, 1650, 1605, 1565, and 1490 cm$^{-1}$.

C. 6-Neopentyl-3-(1H-tetrazol-5-yl)-2-(1H)-pyridinone
(Title Compound of Example 1)

A mixture of 3.8 g of the product of Part B of Example 1 and 1.69 g (26 mmoles) of sodium azide, 1.39 g (26 mmoles) of ammonium chloride, and 40 mg of lithium chloride in 40 ml of dry dimethylformamide is stirred at 125° (oil bath temperature) for 21 hr. The mixture is poured into 200 ml of water, cooled in ice, and acidified with concentrated hydrochloric acid. The solid is collected by filtration, washed with water, dried, and crystallized from acetone-hexane, giving 4.40 g (94%) of product as small buff crystals having a melting point of 251° C. Carbon:Hydrogen:Nitrogen ratio is 56.19:6.41:29.73. Mass spectrum exhibits peaks at 233, 191, 177, 149, 121, 120, 93, 77, 69, 57, and 41. NMR absorptions are observed at 0.98, 2.52, 6.32, and 8.4δ. Infrared absorptions are observed at 3490, 3410, 3340, 3100, 2770, 1655, 1615, 1580, 1525, 1310, 1220, 1035, and 755 cm$^{-1}$.

EXAMPLE 2

1,2-Dihydro-2-oxo-6-t-butyl-3-pyridinecarboxaldehyde
(Formula XIII wherein $R_1$ is t-butyl and $R_2$ is carboxaldehyde)

To a solution of eight g of 1,2-dihydro-2-oxo-6-t-butyl-3-pyridinecarbonitrile and 200 ml of 75% (v/v) aqueous formic acid is added 20 g of Raney nickel. Twenty ml of water is used to assist the addition. The mixture is stirred mechanically and refluxed for one hour. The heat source is then removed. The mixture is stirred at ambient temperature for three hours. The mixture is filtered and the filter cake is washed with 200 ml of warm ethanol and then with 200 ml of water. The combined filtrate and washings is diluted with 700 ml of water and extracted with ethyl acetate (2×500 ml). The combined extracts are washed with 100 ml of water, 100 ml of 10% sodium carbonate solution, and 100 ml of brine and dried over magnesium sulfate. Evaporation of the solvent leaves a yellow oil which appears to contain water or formic acid. Toluene (250 ml) is added and evaporated, leaving 6.24 g of yellow solid. The solid is chromatographed on a 300 g column of silica gel. The column is eluted with 20% acetone-methylene chloride and 200 ml fractions are collected. The fractions are assayed by silica gel tlc (1×4") (ethyl acetate-hexane-acetic acid, 50:50:1). Fractions 4 to 6 are combined and crystallized from methylene chloride hexane solvent system giving 2.47 g (30%) of a product as ivory prisms having a melting point of 192°–195° C. The carbon:hydrogen:nitrogen ratio is 67.05:7.35:7.68. Mass spectrum exhibits peaks at 179, 165, 164, 162, 151, 136, 118, 91, 41 and 39. NMR absorptions are observed at 1.45, 6.39, 8.12, 10.34, and 12.68–13.00δ.

EXAMPLE 3

6-Isobutyl-3-(1H-tetrazol-5-yl)-2-(1H)-pyridinone
(Formula XIII of Chart A—$R_1$ is isobutyl and $R_2$ is tetrazolyl)

A. Sodium Salt of 3-oxo-5-methylhexanal

A mixture of ethyl formate (106 g: 1.43 moles) and methyl isobutyl ketone (1.43 g: 0.43 moles) is added over a 2½ hr period to an ice bath cooled mixture of sodium in small pieces (33 g; 1.43 moles) and diethyl ether (3 l). After stirring for 1½ hr at room temperature, the thick slurry is filtered and then dried to afford 144.76 g, 68% yield of titled product.

B. 1,2-dihydro-6-isobutyl-2-oxo-nicotinonitrile

Two separately prepared solutions are combined with and refluxed for two hours. Solution A is composed of 111.26 g of title product Part A (0.742 moles) cyanoacetamide (54.88 g; 0.653 moles) and water (300 ml). Solution B is composed of glacial acetic acid (8.9 ml) water (22.25 ml) and enough piperidine to make Solution B basic. Glacial acetic acid is used to acidify the cooled reaction mixture. The precipitated product is filtered, washed with water four times and dried. The crystallization from ethanol affords 40.26 g (35%) yield of titled product Part B having a melting point of 147°–150° C. Carbon:Hydrogen:Nitrogen analysis is 68.34:6.89:15.68.

C. 6-Isobutyl-3-(1H-tetrazol-5-yl)-2-(1H)-pyridinone

A mixture of 3.52 g (20 mmoles) of the product of Example 3, Part B, and 1.69 g (26 mmoles) of sodium azide, 1.39 g (26 mmoles) of ammonium chloride, and 28 mg of lithium chloride in 20 ml of dry dimethylformamide is stirred at 120° (oil bath temperature) for 21 hr. The mixture is diluted with 100 ml of water and acidified with concentrated hydrochloric acid. The solid is collected by filtration, washed with water and dried giving 4.17 g of a light brown solid. The solid is crystallized from acetone-tetrahydrofuran-hexane solvent system giving 2.85 g (65%) of title product as tan crystals having a melting point of 260° C. The carbon:hydrogen:nitrogen ratio is 55.04:5.98:31.67. Mass spectrum exhibits peaks at 219, 177, 163, 135, 120, 93, 78, 77, 65, and 51. NMR absorptions are observed at 0.91, 2.01, 2.49, 6.35, 8.408. Infrared absorptions are observed at 3136, 3102, 3060, 2779, 1654, 1616, 1586, 1542, 1481, 1207, 1014, 784, and 767 cm$^{-1}$.

EXAMPLE 4

1,2-Dihydro-2-oxo-6-neopentyl-3-pyridinecarboxaldehyde (Formula XIII—$R_1$ is neopentyl and $R_2$ is carboxaldehyde)

Following the procedure of Example 2, but employing sodium hypophosphite in aqueous acetic acid in pyridine in place of formic acid, the titled product is obtained as crystals with a melting point of 163°–164° C.

CHART A

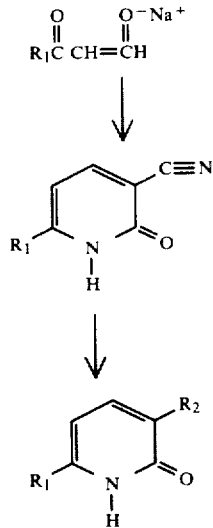

FORMULAS

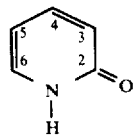

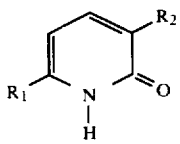

I claim:

1. A 6-alkyl-1,2-dihydro-2-oxo-3-substituted pyridine derivative of the Formula II,

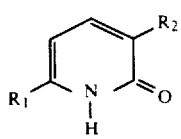

wherein $R_1$ is alkyl of four to eight carbon atoms, inclusive, and $R_2$ is tetrazolyl or carboxaldehyde.

2. 1,2-Dihydro-2-oxo-6-t-butyl-3-pyridinecarboxaldehyde, a compound according to claim 1 wherein $R_1$ is t-butyl and $R_2$ is carboxaldehyde.

3. 6-Neopentyl-3-(1H-tetrazol-5-yl)-2-(1H)-pyridinone, a compound according to claim 1, wherein $R_1$ is neopentyl and $R_2$ is tetrazole.

4. 1,2-Dihydro-2-oxo-6-neopentyl-3-pyridinecarboxaldehyde, a compound according to claim 1 wherein $R_1$ is neopentyl and $R_2$ is carboxaldehyde.

5. 6-Isobutyl-3(1H-tetrazol-5-yl)-2-(1H)pyridinone, a compound according to claim 1, wherein $R_1$ is isobutyl and $R_2$ is tetrazole.

6. A method of treating adult-onset diabetes mellitus in a human suffering from said disease which comprises orally administering an amount of a 6-alkyl-1,2-dihydro-2-oxo-3-substituted pyridine derivative of the Formula II

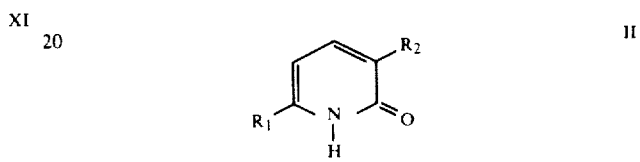

wherein $R_1$ and $R_2$ are as defined in claim 1, effective to exert a predetermined systemic antihyperglycemic effect.

7. A method according to claim 6 wherein said 6-alkyl-1,2-dihydro-2-oxo-3-substituted pyridine is 1,2-dihydro-2-oxo-6-t-butyl-3-pyridinecarboxaldehyde, wherein $R_1$ is t-butyl, and $R_2$ is carboxaldehyde.

8. A method according to claim 6, wherein said 6-alkyl-1,2-dihydro-2-oxo-substituted-3-pyridine is 6-neopentyl-3-(1H-tetrazol-5-yl)-2-(1H)-pyridinone, wherein $R_1$ is neopentyl and $R_2$ is tetrazole.

9. A method according to claim 6 wherein said 6-alkyl-1,2-dihydro-2-oxo-3-substituted pyridine is 1,2-dihydro-2-oxo-6-neopentyl-3-pyridinecarboxaldehyde.

10. A method according to claim 6 wherein said 6-alkyl-1,2-dihydro-2-oxo-substituted-3-pyridine is 6-isobutyl-3-(1H-tetrazol-5-yl)-2-(1H)-pyridinone, wherein $R_1$ is isobutyl and $R_2$ is tetrazole.

11. An oral pharmaceutical composition in unit dosage form comprising an amount of a 6-alkyl-1,2-dihydro-2-oxo-3-substituted-pyridine derivative of Formula II

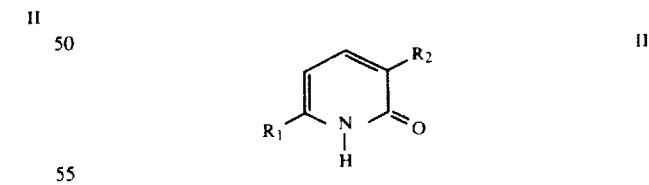

wherein $R_1$, and $R_2$ are as defined in claim 1, sufficient to provide an antihyperglycemic effect in an adult-onset diabetic human to whom said composition is administered.

12. An oral pharmaceutical composition according to claim 11 wherein said 6-alkyl-1,2-dihydro-2-oxo-3-substituted-pyridine is 1,2-dihydro-2-oxo-6-t-butyl-3-pyridinecarboxaldehyde wherein $R_1$ is t-butyl and $R_2$ is carboxaldehyde.

13. An oral pharmaceutical composition according to claim 11 wherein said 6-alkyl-1,2-dihydro-2-oxo-3-substituted-pyridine is 6-neopentyl-3-(1H-tetrazol-5-yl)-2-

(1H)-pyridinone, wherein $R_1$ is neopentyl and $R_2$ is tetrazole.

14. An oral pharmaceutical composition according to claim 11 wherein said 6-alkyl-1,2-dihydro-2-oxo-3-substituted-pyridine is 1,2-dihydro-2-oxo-6-neopentyl-3-pyridinecarboxaldehyde wherein $R_1$ is neopentyl and $R_2$ is carboxaldehyde.

15. An oral pharmceutical composition according to claim 11, wherein said 6-alkyl-1,2-dihydro-2-oxo-3-substituted-pyridine is 6-isobutyl-3-(1H-tetrazol-5-yl)-2-(1H)-pyridinone, wherein $R_1$ is isobutyl and $R_2$ is tetrazole.

* * * * *